US006867011B1

(12) United States Patent
Babin et al.

(10) Patent No.: US 6,867,011 B1
(45) Date of Patent: Mar. 15, 2005

(54) SYNTHETIC BIOEPITOPE COMPOUNDS WHICH CAN BE USED AS STANDARDS IN THE BIOLOGICAL ASSAYS OF TROPONIN I

(75) Inventors: Fabienne Noelle Babin, Montigny le Bretonneux (FR); Charles Didier Calzolari, Lyons (FR); Odile Suzanne Helene Flecheux, Viroflay (FR); Claude Granier, Clapiers (FR); Catherine Christiane Marie Larue, Montpellier (FR); Bernard Christian Pau, Montpellier (FR); Francois Yves Rieunier, Fontenay le Fleury (FR); Sylvie Marie-France Trinquier, Marguerittes (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 0 days.

(21) Appl. No.: 09/308,671

(22) PCT Filed: Dec. 4, 1997

(86) PCT No.: PCT/FR97/02209

§ 371 (c)(1),
(2), (4) Date: Oct. 12, 1999

(87) PCT Pub. No.: WO98/24816

PCT Pub. Date: Jun. 11, 1998

(30) Foreign Application Priority Data

Dec. 5, 1996 (FR) .......................................... 96 14959

(51) Int. Cl.$^7$ ........................ G01N 33/535; C07K 1/13
(52) U.S. Cl. ............................ 435/7.92; 436/8; 436/15; 435/967; 530/300; 530/402

(58) Field of Search ................. 435/7.92–7.95, 435/7.1, 4, 967; 436/1, 2, 8, 15, 18; 530/300, 402

(56) References Cited

U.S. PATENT DOCUMENTS

| 5,846,738 A | * | 12/1998 | Seidel et al. ................. 435/7.1 |
| 6,072,040 A | * | 6/2000 | Dave et al. ................. 530/412 |
| 6,077,676 A | * | 6/2000 | Shi et al. ..................... 435/7.1 |
| 6,165,981 A | * | 12/2000 | Flaa et al. ..................... 514/21 |

FOREIGN PATENT DOCUMENTS

| DE | 42 43 648 A | | 7/1994 | .......... C07K/15/28 |
| EP | 0 650 053 A | | 4/1995 | .......... G01N/33/53 |
| WO | WO 94 27156 A | | 11/1994 | .......... G01N/33/68 |
| WO | WO 96 27661 A | | 9/1995 | ............. C12N/9/96 |
| WO | WO 97/39132 | * | 10/1997 | .......... C12N/15/62 |

OTHER PUBLICATIONS

Morjana et al., *FASEB Journal*, vol. 10, No. 6, Apr. 30, 1996, p. A–1295, "Biochemical and Immunological Properties of a Cyanogem Bromide Fragment of Human Cardiac Troponin I".

Vallins et al., *FEBS Letters*, vol. 270, No. ½, Sep. 1990, pp. 57–61, "Molecular cloning of human cardiac troponin I using polymerase chain reaction".

* cited by examiner

*Primary Examiner*—Mary E. Ceperley
*Assistant Examiner*—Ann Y. Lam
(74) *Attorney, Agent, or Firm*—Jacobson Holman PLLC

(57) ABSTRACT

The invention relates to synthetic biepitope compounds which can be used as standards in immunoassays, for the assay of troponin I, method for preparing them, compositions and kits containing such compounds as well as the immunoassay methods using such compounds.

10 Claims, No Drawings

SEQUENCE LISTING

<160> NUMBER OF SEQ ID NOS: 74

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Glu Pro His
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ala Lys Lys
  1

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ala Pro Ile Arg Arg Arg
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Gly Ala Arg
  1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Lys Asn Ile
  1

<210> SEQ ID NO 6
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Gln Lys Met Gln
  1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gly Pro Asp Asn
  1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Pro Asp Asn
  1

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Met Met Lys Ser Lys Gln Lys Met Gln
  1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Lys Lys Ala Met Met Lys Ser Lys Gln Lys Met Gln
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Met Met Lys Ser Lys Gln Lys Met Gln Gln Ala
  1               5                  10
```

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Lys Lys Ala Met Met Lys Ser Lys Gln Lys Met Gln Gln Ala
 1               5                  10                  15

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ser Lys Gln Lys Met Gln Ala Met Met
 1               5                  10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Lys Lys Lys Ser Lys Gln Lys Met Gln Ala Met Met
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ser Lys Gln Lys Met Gln Ala Met Met Gln Ala
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Lys Lys Lys Ser Lys Gln Lys Met Gln Ala Met Met Gln Ala
 1               5                  10                  15

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 17

Ala Met Met
 1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Lys Lys Ala Met Met
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Met Met Gln Ala
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Lys Lys Ala Met Met Gln Ala
 1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Gly Asn Ser
 1

<210> SEQ ID NO 22
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Lys NH-(CH2)5-CO

<400> SEQUENCE: 22

Ala Lys Lys
 1
```

```
<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ala NH-(CH2)5-CO

<400> SEQUENCE: 23

Ala Met Met
 1

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Lys NH-(CH2)5-CO

<400> SEQUENCE: 24

Ala Lys Lys Ala Met Met
 1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ala NH-(CH2)5-CO

<400> SEQUENCE: 25

Ala Met Met Gln Ala
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Lys NH-(CH2)5-CO

<400> SEQUENCE: 26

Ala Lys Lys Ala Met Met Gln Ala
 1               5

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Asn Tyr Arg Ala Tyr Ala Thr Glu Pro His Ala Lys Lys Ala Met
```

-continued

```
                1               5                  10                  15
Met Gln Ala Leu Leu Gly Ala Arg Ala Lys Glu
                20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (14)
<223> OTHER INFORMATION: Lys NH-(CH2)5-CO

<400> SEQUENCE: 28

Gly Asn Tyr Arg Ala Tyr Ala Thr Glu Pro His Ala Lys Lys Ala Met
 1               5                  10                  15

Met Gln Ala Leu Leu Gly Ala Arg Ala Lys Glu
                20                  25

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Tyr Arg Ala Tyr Ala Thr Glu Pro His Ala Lys Lys Lys Ser Lys
 1               5                  10                  15

Gln Lys Met Gln Ala Met Met Gln Ala Leu Leu Gly Ala Arg Ala Lys
                20                  25                  30

Glu

<210> SEQ ID NO 30
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Asn Tyr Arg Ala Tyr Ala Thr Glu Pro His Ala Lys Lys Lys
 1               5                  10                  15

Ser Lys Gln Lys Met Gln Ala Met Met Gln Ala Leu Leu Gly Ala Arg
                20                  25                  30

Ala Lys Glu
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Asn Tyr Arg Ala Tyr Ala Thr Glu Pro His Ala Lys Lys Lys
 1               5                  10                  15

Ser Lys Gln Lys Met Gln Gln Lys Met Gln Ala Met Met Gln Ala Leu
```

```
                    20                  25                  30

Leu Gly Ala Arg Ala Lys Glu
            35

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Asn Tyr Arg Ala Tyr Ala Thr Glu Pro His Ala Lys Lys Lys Ser
 1               5                  10                  15

Lys Gln Lys Met Gln Gln Lys Met Gln Ala Met Met Gln Ala Leu Leu
            20                  25                  30

Gly Ala Arg Ala Lys Glu
            35

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Pro Ala Pro Ala Pro Ile Arg Arg Arg Pro Gly Asn Ser Thr Glu
 1               5                  10                  15

Pro His Ala Lys Lys Lys Ser Lys
            20

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ala Ala Arg Glu
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Arg Ser Ser
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 36

Tyr Arg Ala Tyr Ala Thr Glu Pro
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Ser Ala Ser Arg Lys Leu Gln Leu Lys
 1               5                  10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Lys Gln Glu Leu Glu
 1               5

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Glu Leu Gln
 1

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Gln Asp Leu Cys Arg
 1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Leu Thr Gln Lys Ile Phe Asp Leu Arg
 1               5                  10

<210> SEQ ID NO 42
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 42

Pro Thr Leu Arg Arg Val Arg
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Asp Ala Met Met Gln Ala
 1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Leu Leu Gly
 1

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Leu Asp Leu Arg Ala His
 1               5

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Asn Arg Glu
 1

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Trp Arg Lys Asn Ile Asp
 1               5
```

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Glu Pro His Ala Lys Lys
  1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ala Leu Leu Gly Ala Arg
  1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Thr Leu Arg Arg Val Arg Ile Ser Ala
  1               5                  10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Lys Phe Lys Arg Pro Thr Leu Arg Arg Val Arg
  1               5                  10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gly Phe Ala Glu Leu Gln Asp
  1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 53

Asn Tyr Arg Ala Tyr Ala Thr Glu Pro His
 1               5                  10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Tyr Ala Thr Glu Pro His
 1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Gly Phe Ala Glu Leu Gln
 1               5

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Ser Lys
 1

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Asn Tyr Arg Ala Tyr Ala
 1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Asn Tyr Arg Ala Tyr Ala
 1               5

<210> SEQ ID NO 59
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Tyr Arg Ala Tyr Ala
 1               5

<210> SEQ ID NO 60
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Pro Ala
 1

<210> SEQ ID NO 61
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Lys Glu
 1

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Lys Lys Lys Ser Lys
 1               5

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (15)
<223> OTHER INFORMATION: Lys NH-(CH2)5-CO

<400> SEQUENCE: 63

Cys Gly Asn Tyr Arg Ala Tyr Ala Thr Glu Pro His Ala Lys Lys Ala
 1               5                  10                  15
Met Met Gln Ala Leu Leu Gly Ala Arg Ala Lys Glu
                20                  25

<210> SEQ ID NO 64
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 64

Gly Asn Tyr Arg Ala Tyr Ala Ala Lys Lys Ala Met Met Gln Ala Ala
 1               5                  10                  15

Lys Glu

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (10)
<223> OTHER INFORMATION: Lys NH-(CH2)5-CO

<400> SEQUENCE: 65

Gly Asn Tyr Arg Ala Tyr Ala Ala Lys Lys Ala Met Met Gln Ala Ala
 1               5                  10                  15

Lys Glu

<210> SEQ ID NO 66
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Asn Tyr Arg Ala Tyr Ala Ala Lys Lys Ala Met Met Lys Ser
 1               5                  10                  15

Lys Gln Lys Met Gln Gln Lys Met Gln Gln Ala Ala Lys Glu
             20                  25                  30

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Asn Tyr Arg Ala Tyr Ala Ala Lys Lys Ala Met Met Lys Ser
 1               5                  10                  15

Lys Gln Lys Met Gln Gln Ala Ala Lys Glu
             20                  25

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Tyr Arg Ala Tyr Ala Ala Lys Lys Ala Met Met Lys Ser Lys Gln
 1               5                  10                  15

Lys Met Gln Gln Ala Ala Lys Glu
             20
```

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Asn Tyr Arg Ala Tyr Ala Ala Lys Lys Lys Ser Lys Gln Lys Met Gln
 1               5                  10                  15

Ala Met Met Gln Ala Ala Lys Glu
            20

<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Gly Gly Asn Tyr Arg Ala Tyr Ala Ala Lys Lys Lys Ser Lys Gln Lys
 1               5                  10                  15

Met Gln Ala Met Met Gln Ala Ala Lys Glu
            20                  25

<210> SEQ ID NO 71
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Gly Gly Asn Tyr Arg Ala Tyr Ala Ala Lys Lys Lys Ser Lys Gln Lys
 1               5                  10                  15

Met Gln Gln Lys Met Gln Ala Met Met Gln Ala Ala Lys Glu
            20                  25                  30

<210> SEQ ID NO 72
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Gly Asn Tyr Arg Ala Tyr Ala Ala Lys Lys Ser Lys Gln Lys Met
 1               5                  10                  15

Gln Gln Lys Met Gln Ala Met Met Gln Ala Ala Lys Glu
            20                  25

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<221> NAME/KEY: MOD_RES
<222> LOCATION: (11)

```
<223> OTHER INFORMATION: Lys NH-(CH2)5-CO

<400> SEQUENCE: 73

Cys Gly Asn Tyr Arg Ala Tyr Ala Ala Lys Lys Ala Met Met Gln Ala
 1               5                  10                  15

Ala Lys Glu

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<400> SEQUENCE: 74
Arg Pro Ala Pro Gly Asn Ser Ala Lys Lys Lys Ser Lys
 1               5                  10
```

SYNTHETIC BIOEPITOPE COMPOUNDS WHICH CAN BE USED AS STANDARDS IN THE BIOLOGICAL ASSAYS OF TROPONIN I

This application is a 371 of PCT/FR97/02209 filed Dec. 4, 1997.

The present invention relates to synthetic biepitope compounds which can be used as standards in immunoassays, for the assay of troponin I, method for preparing them, compositions and kits containing such compounds as well as immunoassay methods using such compounds.

It is known that troponin is a myofibrillar protein complex consisting of three proteins, troponins I, T and C. This protein complex makes it possible to contribute to the regulation of muscle contraction by the $Ca^{2+}$ ion by interacting with myosin and actin. More precisely, it is known that when a nerve impulse arrives at the level of the motor endplate of a muscle, there is generation of an action potential which is transmitted to the sarcoplasmic reticulum. $Ca^{2+}$ is then released into the cytosol and binds to troponin C, which brings about a strengthening of the interaction between troponin I and troponin C and, consequently, a change in conformation of the troponin I, T, C complex. There is then liberation of the sites of actin-myosin interaction, which allows the muscle contraction movement.

When the muscle is damaged, whether it is the cardiac muscle, during myocardial necrosis following a myocardial infarction, or whether it is the skeletal muscle during sustained physical effort, the troponins then released appear more or less rapidly in the blood stream.

Thus, the assay of troponin has recently been recommended for the early diagnosis of myocardial infarction, whether that of troponin T in *Circulation* (1991,) 8, pp. 902–912, or of troponin I in *Am. Heart J.* (1987), 110, pp. 1333–1344, and *Molecular Immunology* (1992), 29 f 2), pp. 271–278. Likewise, the assay of cardiac troponin T for measuring the success of thrombolytic therapy following a myocardial infarction has been proposed in *Br. Heart J.*, (1994), 7, pp. 242–248, as well as the assay of skeletal troponin I for the measurement of damage to the skeletal muscles (abstract No. 35 of the *American Association for Clinical Chemistry*, 46th National Meeting, New Orleans, Jul. 17–21, 1994). It should be noted that the assay of the various cardiac and skeletal troponins is nowadays a very useful means for the diagnosis of human and animal pathologies.

It is well known that the immunoassays performed in biological analysis laboratories require the supply by the manufacturer, besides the reagents necessary for the assay (that is to say antibodies, labelled or otherwise, revealing agents and diluting solutions), of a standard for the compound to be determined which, used under conditions similar to those of the sample to be studied, will serve as reference for calculating the results and/or as positive control.

To obtain the standard and/or the control for the compound to be determined, it is possible to use the said compound purified in freeze-dried form (accompanied by a solvent in which the compound will be dissolved by the user before use) or ready for use.

Because biological reagents are unstable, the standard or control solutions prepared from a freeze-dried product are frozen in unit doses and stored at −80° C. It has been observed, moreover, that these solutions were not stable for more than a few hours at +4° C., even if protease inhibitors or antibacterial agents were added to them. This therefore requires the users to prepare their standard solutions immediately before use.

The patent application published under the number FR-A-2,701,954 discloses a stabilized solution of troponin I or T for immunoassay, characterized in that it consists of an aqueous solution containing troponin I or troponin T, mixed with troponin C and particularly in proportions of 1 to 10 molar equivalents of troponin C per equivalent of troponin I or T, and calcium chloride. This technique allows preservation for several days at +4° C. of standard solutions, diluted to a greater or lesser extent, of troponin I or T.

The patent application published under the number FR 2,734,267 describes standard solutions of troponin composed of a ternary complex formed by troponin I, troponin T and troponin C.

The raw materials used to obtain these standards are of human or animal origin, and the standards or controls thus obtained are stable for about one month at +4° C.

Application WO 94/15217 describes some synthetic peptides useful as immunogens for the preparation of antibodies recognizing the N-terminal peptide of troponin I. Some of these peptides can be used as standards in immunoassays of troponin I, using the antibodies which are the subject of the invention covered by application WO 94/15217.

Likewise, patent application WO 94/27156 relates to a method of assaying cardiac troponin I, using antibodies specific for cardiac troponin I. These antibodies can be prepared from peptide fragments having a sequence absent from skeletal muscle troponin I and therefore specific for cardiac troponin I. However, this application neither discloses nor suggests the possibility of using certain peptide fragments as standards in immunoassays of troponin I.

It is also known that application WO 96/27661 describes aqueous solutions for stabilizing proteins and peptides. These solutions find application in particular in diagnostic tests for proteins or peptides.

According to WO 97/27661, these aqueous solutions even make it possible to increase the stability of the fragments of troponin I which are known to be less stable than whole troponin I.

Application EP-A-752 426 published on 8 Jan. 1997 also describes troponin I standards composed of one or more peptides bound to a carrier molecule such as high-molecular weight proteins (>100 KD) or polymers.

Application EP-A-650 053 describes synthetic standards containing active sites for one or more receptors, linked to each other with an arborescent structure. This application describes more particularly synthetic standards for troponin T which are stable in solution for only 3 weeks.

It has now been found that it is possible to obtain synthetic standards which can be used for the evaluation of troponin I, which are stable for several months.

Indeed, the specific structure of the compounds of the invention confer an excellent stability on them.

The compounds of the present invention therefore make it possible to obtain highly standardized standards, which are stable in solution for several months, and to avoid the purification steps and the complex extraction procedures which are necessary for the preparation of troponin I standards from animal organs.

The compounds of the invention comprise two epitopes of troponin I, linked to each other by a linker and correspond to the general formula I:

$$\Xi\text{-}E_1\text{-}Z\text{-}E_2\text{-}\Psi \quad (I)$$

in which:

$E_1$, and $E_2$, which are identical or different, represent a peptide sequence comprising either a minimum epitope of troponin I, or an extended epitope, Z represents a peptide sequence of 1 to 40 amino acids (aa), provided however that $-E_1$-Z-$E_2$ - do not form together a portion of the troponin I sequence, a linear or branched amino($C_1$–$C_{10}$ alkyl)carbonyl chain, or a mixed construct consisting of at least one peptide sequence of 1 to 10 amino acids and at least one linear or branched amino($C_1$–$C_{10}$ alkyl)carbonyl chain, Ξ represents a hydrogen atom, an acetyl group, a peptide sequence of 1 to 10 amino acids, an N-α-acetylated peptide sequence of 1 to 10 amino acids, a cysteinyl, biotinyl or biocytinyl group, a peptide sequence of 1 to 10 amino acids carrying a cysteinyl, biotinyl or biocytinyl residue, a linear or branched amino($C_1$–$C_{10}$ alkyl)carbonyl chain, an N-α-acetylated linear or branched amino($C_1$–$C_{10}$ alkyl)carbonyl chain, a mixed construct consisting of at least one peptide sequence of 1 to 10 amino acids and at least one linear or branched amino($C_1$–$C_{10}$ alkyl)carbonyl chain, or a mixed construct consisting of at least one peptide sequence of 1 to 10 amino acids and at least one linear or branched amino($C_1$–$C_{10}$ alkyl)carbonyl chain carrying a biotinyl, biocytinyl or cysteinyl residue, Ψ represents a hydroxyl radical, an amino radical, a peptide sequence of 1 to 10 amino acids, a peptide sequence of 1 to 10 amino acids carrying an amino-terminal group, a linear or branched amino($C_1$–$C_{10}$ alkyl)carbonyl chain, a linear or branched amino($C_1$–$C_{10}$ alkyl)carbonyl chain carrying a hydroxyl radical or an amino radical, a mixed construct consisting of at least one peptide sequence of 1 to 10 amino acids and at least one linear or branched amino($C_1$–$C_{10}$ alkyl)carbonyl chain, a mixed construct consisting of at least one peptide sequence of 1 to 10 amino acids and at least one linear or branched amino($C_1$–$C_{10}$ alkyl)carbonyl chain carrying a hydroxyl radical or an amino radical.

It is considered that $-E_1$-Z-$E_2$ - is not a portion of the troponin I sequence when $-E_1$-Z-$E_2$ - differs from a given fragment of the troponin I sequence by a nonconservative substitution, deletion or insertion of at least one amino acid, preferably of 2 amino acids, more particularly of 5 amino acids.

Z may in particular represent a chain of formula II:

$$—NH—(CH_2)_m—CO— \quad (II)$$

in which m represents an integer from 1 to 10, or a mixed construct of formulae III to V:

$$-[pep_1\text{-}NH—(CH_2)_m—CO]_p\text{-} \quad (III)$$

$$-[pep_1\text{-}NH—(CH_2)_m—CO\text{-}pep_2]_p\text{-} \quad (IV)$$

$$-[NH—(CH_2)_m—CO\text{-}pep_2]_p\text{-} \quad (V)$$

in which m represents an integer from 1 to 10, p represents an integer from 1 to 5, and $pep_1$ and $pep_2$, which are identical or different, represent a peptide chain containing from 2 to 10 amino acids;

Ξ may in particular represent a chain of formula IIa:

$$—NH—(CH_2)_q—CO— \quad (IIa)$$

in which q represents an integer from 1 to 10, or a mixed construct of formulae IIIa to Va:

$$-[pep_3\text{-}NH—(CH_2)_q—CO]_r\text{-} \quad (IIIa)$$

$$-[pep_3\text{-}NH—(CH_2)_q—CO\text{-}pep_4]_r\text{-} \quad (IVa)$$

$$-[NH—(CH_2)_q—CO\text{-}pep_4]_R\text{-} \quad (Va)$$

in which q represents an integer from 1 to 10, r represents an integer from 1 to 5, and $pep_3$ and $pep_4$, which are identical or different, represent a peptide chain containing from 2 to 10 amino acids, an N-α-acetylated chain of formulae IIa to Va, or a chain of formulae IIa to Va carrying a biotinyl, biocytinyl or cysteinyl residue; and Ψ may in particular represent a chain of formula IIb:

$$—NH—(CH_2)_s—CO— \quad (IIb)$$

in which s represents an integer from 1 to 10, or a mixed construct of formulae IIIb to Vb:

$$-[pep_5\text{-}NH—(CH_2)_s—CO]_t\text{-} \quad (IIIb)$$

$$-[pep_5\text{-}NH—(CH_2)_s—CO\text{-}pep_6]_t\text{-} \quad (IVb)$$

$$-[NH—(CH_2)_s—CO\text{-}pep_6]_t\text{-} \quad (Vb)$$

in which s represents an integer from 1 to 10, t represents an integer from 1 to 5, and $pep_5$ and $pep_6$, which are identical or different, represent a peptide chain containing from 2 to 10 amino acids, a chain of formulae IIb to Vb carrying a hydroxyl radical or an amino radical.

Among the preferred compounds of the invention are the compounds in which Ξ represents either a chain of formula IIa, or a mixed construct IIIa to Va, or an N-α-acetylated chain of formulae IIa to Va or a chain of formulae IIa to Va carrying a biotinyl, biocytinyl or cysteinyl residue.

Among the preferred compounds of the invention are also the compounds in which Ψ represents either a chain of formula IIb, or a mixed construct of formulae IIIb to Vb, or a chain of formulae IIb to Vb carrying a hydroxyl radical or an amino radical.

The compounds of the invention in which Z represents either a chain of formula II or a mixed construct of formulae III to V are preferred in particular.

The peptide sequences comprising a minimum epitope of troponin I have been determined with the aid of anti-troponin I monoclonal antibodies. Such antibodies are described by Larue et al. (*Molec. Immunology*, (1992), vol. 20 No. 29, pp. 271–278), Bodor et al. (*Clin. Chem.* (1992), vol 38 No. 11, pp. 2203–2214), Granier et al (*Protein Science, (1997), vol. 6 suppl. 1. p. 61) and in application WO 94/15217. The majority of these antibodies are commercially available (Hytest LTD-Turku, Finland).

To determine the peptide sequence comprising a minimum epitope of troponin I, the simultaneous synthesis of peptides of 10 amino acids, in which the sequence overlaps with the sequence of the preceding peptide by 7 amino acids, was carried out according to the following scheme:

Peptide 1=amino acids 1–10
Peptide 2=amino acids 4–13
Peptide 3=amino acids 7–16
etc.

As a whole, the peptides synthesized and tested describe the entire sequence of the protein (Vallins J. et al., *FEBS Letters* (1990), vol. 270 No. 1–2, pp. 57–61).

The peptides which react with each of the monoclonal antibodies used were then identified by an immunoenzymatic test for binding of each peptide with each antibody.

Indicated for example below, for some anti-troponin I monoclonal antibodies, are the peptide sequence comprising a minimum epitope immunologically reactive for each antibody and the position of this peptide sequence in the troponin I sequence, as described in *FEBS Letters* (1990), vol. 270 No. 1–2, pp. 57–61.

| Antibody | Epitope* | Position in the troponin I sequence |
|---|---|---|
| 5C3 (SEQ ID NO:34) | DAARE | 7–11 |
| 10B11 (SEQ ID NO:3) | PAPIRRR | 16–22 |
| HC11 (SEQ ID NO:35) | RRRSS | 20–24 |
| HG5 and HC2 (SEQ ID NO:36) | YRAYATEP | 26–33 |
| 11E12 (SEQ ID NO:1) | TEPH | 31–34 |
| 10F4 (SEQ ID NO:2) | HAKK | 34–37 |
| HC7 (SEQ ID NO:37) | ISASRKLQLK | 41–50 |
| H414 (SEQ ID NO:38) | AKQELE | 57–62 |
| 5F1 (SEQ ID NO:39) | AELQ | 91–94 |
| 13H7 and 20C5 (SEQ ID NO:40) | LQDLCR | 93–98 |
| 2B7 (SEQ ID NO:41) | DLTQKIFDLR | 127–136 |
| 3G11 and 15F2 (SEQ ID NO:42) | PTLRRVR | 142–148 |
| 2E6 and 8G2 (SEQ ID NO:43) | ADAMMQA | 151–157 |
| 7D1 (SEQ ID NO:44) | ALLG | 157–160 |
| 8E1 (SEQ ID NO:4) | LLGAR | 158–162 |
| 9E8 (SEQ ID NO:45) | SLDLRAH | 166–172 |
| 4B5 (SEQ ID NO:46) | ENRE | 184–187 |
| 7F4 (SEQ ID NO:47) | DWRKNID | 190–196 |

*The peptide sequences are indicated using a single-letter code.

The peptide sequences derived from the said peptide sequences by substitution, deletion or insertion of an amino acid also belong to the field of the invention since they exhibit equivalent affinity for binding to the antibody.

The following linear sequences $E_1$ and/or $E_2$ No. 1 to 5 are preferred.

(SEQ ID NO:1): -Thr Glu Pro His- or -TEPH- (SEQ ID NO:2): -His Ala Lys Lys- or -HAKK- (SEQ ID NO:3): -Pro Ala Pro Ile Arg Arg Arg- or -PAPIRRR- (SEQ ID NO:4): -Leu Leu Gly Ala Arg- or -LLGAR- (SEQ ID NO:5): -Arg Lys Asn Ile- or -RKNI-.

The above sequences are given by way of a non-limiting example.

When the linker Z comprises a peptide sequence, the latter may form with the sequences $E_1$ and/or $E_2$ an extended epitope of troponin I. This extended epitope may in particular have a sequence (SEQ ID NOS 48–55 respectively, in order of appearance); -TEPHAKK- or -QALLGAR- or -PTLRRVRISA- or -GKFKRPTLRRVR- or -LGFAELQD- or -NYRAYATEPH- or -AYATEPH- or -LGFAELQ-, etc.

These extended epitopes, which amplify the immunological response for antibodies were determined by adding amino acids to the peptide sequence comprising a minimum epitope determined as described above.

As has been shown above, the peptide sequence of the linker Z may comprise from 1 to 40 amino acids. It is preferable that the number of amino acids which form the peptide sequence of Z is less than 30, more particularly less than 20.

A particularly preferred peptide sequence of Z includes a sequence selected from the following amino acid sequences (SEQ ID NOS 6, 8, 17, 22, 56, & 21, respectively, in order of appearance):

-Gln Lys Met Gln- or -QKMQ-,

-Gly Pro Asp Asn- or -GPDN-,

-Ala Met Met- or -AMM-,

-Ala Lys Lys- or -AKK-,

-Lys Ser Lys- or -KSK-, and

-Pro Gly Asn Ser- or -PGNS-.

This particularly preferred peptide sequence of Z may contain a repeated stretch of amino acids and has a number of amino acids less than 30.

By way of example, there are given the Z peptide sequences of the following formulae in which n represents an integer from 1 to 5:

(SEQ ID NO:6): -Gln Lys Met Gln-
or -QKMQ- (SEQ ID NO:7): -Gln Gly Pro Asp Asn-
or -QGPDN- (SEQ ID NO:8): -Gly Pro Asp Asn-
or -GPDN- (SEQ ID NO:9): Ala Met Met Lys Ser Lys (Gln Lys Met Gln)$_n$-
or -AMMKSK-(QKMQ)$_n$-

(SEQ ID NO:10): -Ala Lys Lys Ala Met Met Lys Ser Lys-(Gln Lys Met Gln)$_n$-
or -AKKAMMKSK-(QKMQ)$_n$-

(SEQ ID NO:11): -Ala Met Met Lys Ser Lys-(Gln Lys Met Gln)$_n$-Gln Ala-

-continued or -AMMKSK-(QKMQ)$_n$-QA- (SEQ ID NO:12): -Ala Lys Lys Ala Met Met Lys Ser Lys-(Gln Lys Met Gln)$_n$-Gln Ala-
or -AKKAMMKSK-(QKMQ)$_n$-QA- (SEQ ID NO:13): -Lys Ser Lys-(Gln Lys Met Gln)$_n$-Ala Met Met-
or -KSK-(QKMQ)$_n$-AMM- (SEQ ID NO:14): -Ala Lys Lys Lys Ser Lys-(Gln Lys Met Gln)$_n$-Ala Met Met-
or -AKKKSK-(QKMQ)$_n$-AMM- (SEQ ID NO:15): -Lys Ser Lys-(Gln Lys Met Gln)$_n$-Ala Met Met Gln Ala-
or -KSK-(QKMQ)$_n$-AMMQA- (SEQ ID NO:16): -Ala Lys Lys Lys Ser Lys-(Gln Lys Met Gln)$_n$-Ala Met Met Gln Ala-
or -AKKKSK-(QKMQ)$_n$-AMMQA- (SEQ ID NO:17): -Ala Met Met-
or -AMM- (SEQ ID NO:18): -Ala Lys Lys Ala Met Met-
or -AKKAMM- (SEQ ID NO:19): -Ala Met Met Gln Ala-
or -AMMQA- (SEQ ID NO:20): -Ala Lys Lys Ala Met Met Gln Ala-
or - AKKAMMQA- (SEQ ID NO:21): -Pro Gly Asn Ser-
or -PGNS- Z may also represent a mixed construct of formulae III to V, in which m is an integer from 1 to 10.

By way of a non-limiting example, Z may thus correspond to the following sequences:

(SEQ ID NO:22) -Ala Lys Lys-NH-(CH$_2$)$_m$-CO-
or -AKK-NH-(CH$_2$)$_m$-CO- (SEQ ID NO:23) -NH-(CH$_2$)$_m$-CO-Ala Met Met-
or -NH-(CH$_2$)$_m$-CO-AMM- (SEQ ID NO:24) -Ala Lys Lys-NH-(CH$_2$)$_m$-CO-Ala Met Met-
or -AKK-NH-(CH$_2$)$_m$-CO-AMM- (SEQ ID NO:25) -NH-(CH$_2$)$_m$-CO-Ala Met Met Gln Ala-
or -NH-(CH$_2$)$_m$-CO-AMMQA- (SEQ ID NO:26) -Ala Lys Lys-NH-(CH$_2$)$_m$-CO-Ala Met Met Gln Ala-
or -AKK-NH-(CH$_2$)$_m$-CO-AMMQA-

Preferred compounds of the present invention are the biepitope compounds of formula I, in which Z includes a sequence selected from the sequences No. 6 to 26, as defined above.

When Ξ and/or Ψ contain a peptide sequence, this sequence may form an extended epitope with $E_1$ and/or $E_2$ with which it is linked.

Advantageously, the chemical structure of Ξ is such that it allows the binding of the biepitope compounds of the invention to a natural carrier protein, to a peptide construct or to a solid phase.

The synthetic biepitope peptides of formula Ia and Ib form part of the peptides of formula I and are preferred peptides: (These formula peptides are encompassed by various peptide sequences listed throughout the application, including those peptides disclosed in the tables shown on page 14.);

Ξ-Thr Glu Pro His-Z-Leu Leu Gly Ala Arg-Ψ        (Ia)

Ξ-Pro Ala Pro Ile Arg Arg Arg-Z-Thr Glu Pro His-Ψ     (Ib)

In the formulae Ia and Ib:

Z includes or represents a sequence selected from the following sequences:

(SEQ ID NO: 6): -Gln Lys Met Gln- (SEQ ID NO: 7): -Gln Gly Pro Asp Asn- (SEQ ID NO: 8): -Gly Pro Asp Asn- (SEQ ID NO: 20): -Ala Met Met Gln Ala- (SEQ ID NO: 26): -Ala Lys Lys-NH-(CH$_2$)$_m$-CO-Ala Met Met Gln Ala (SEQ ID NO: 12): -Ala Lys Lys Ala Met Met Lys Ser Lys-(Gln Lys Met Gln)$_n$-Gln Ala- (SEQ ID NO: 16): -Ala Lys Lys Lys Ser Lys-(Gln Lys Met Gln)n-Ala Met Met Gln Ala- (SEQ ID NO: 21): -Pro Gly Asn Ser-, in which n represents an integer from 1 to 5 and m an integer from 1 to 10, Ξ represents an acetyl radical, a cysteinyl radical, a biotinyl or biocytinyl radical optionally linked with the residue of a peptide sequence comprising a sequence selected from the following sequences: (SEQ ID NOS 57–60, respectively, in order of appearance);

-Gly Asn Tyr Arg Ala Tyr Ala-

-Gly Gly Asn Tyr Arg Ala Tyr Ala-

-Asn Tyr Arg Ala Tyr Ala-, and

-Arg Pro Alaand

Ψ represents an amino radical or a peptide sequence comprising one of the following sequences: (SEQ ID NOS 61–62, respectively, in order of appearance);

-Ala Lys Glu

-Ala Lys Lys Lys Ser Lys.

Any peptide including one of the sequences 27 to 33, which are the following, is preferred:

(SEQ ID NO:27)
-Gly Asn Tyr Arg Ala Tyr Ala Thr Glu Pro His Ala Lys Lys Ala Met Met Gln Ala Leu
   1               5                  10                 15                  20
Leu Gly Ala Arg Ala Lys Glu-
              25

(SEQ ID NO:28)
-Gly Asn Tyr Arg Ala Tyr Ala Thr Glu Pro His Ala Lys Lys -NH-(CH$_2$)$_5$-CO-Ala Met
   1               5                  10                         15                 17
Met Gln Ala Leu Leu Gly Ala Arg Ala Lys Glu-
          20                  25

(SEQ ID NO:29)
-Asn Tyr Arg Ala Tyr Ala Thr Glu Pro His Ala Lys Lys Lys Ser Lys Gln Lys Met Gln
   1               5                  10                 15                  20
Ala Met Met Gln Ala Leu Leu Gly Ala Arg Ala Lys Glu-
              25                  30

(SEQ ID NO:30)
-Gly Gly Asn Tyr Arg Ala Tyr Ala Thr Glu Pro His Ala Lys Lys Lys Ser Lys Gln Lys
   1               5                  10                 15                  20
Met Gln Ala Met Met Gln Ala Leu Leu Gly Ala Arg Ala Lys Glu-
              25                  30                  35

(SEQ ID NO:31)
-Gly Gly Asn Tyr Arg Ala Tyr Ala Thr Glu Pro His Ala Lys Lys Lys Ser Lys Gln Lys
   1               5                  10                 15                  20
Met Gln Gln Lys Met Gln Ala Met Met Gln Ala Leu Leu Gly Ala Arg Ala Lys Glu-
              25                  30                  35

(SEQ ID NO:32)
-Gly Asn Tyr Arg Ala Tyr Ala Thr Glu Pro His Ala Lys Lys Lys Ser Lys Gln Lys Met
   1               5                  10                 15                  20
Gln Gln Lys Met Gln Ala Met Met Gln Ala Leu Leu Gly Ala Arg Ala Lys Glu-
              25                  30                  35

(SEQ ID NO:33)
-Arg Pro Ala Pro Ala Pro Ile Arg Arg Pro Gly Asn Ser Thr Glu Pro His Ala Lys
   1               5                  10                 15                  20
Lys Lys Ser Lys-

The synthetic biepitope peptides of formula Ia and Ib below are particularly preferred peptides. In the two tables which follow, the peptide sequences are given using the single-letter code.

| | Ξ-TEPH-Z-LLGAR-Ψ   (Ia) | | |
|---|---|---|---|
| COMPOUND | Ξ- | -Z- | -Ψ |
| 1 (SEQ ID NO:6) | Ac- | -QKMQ- | -NH$_2$ |
| 2 (SEQ ID NO:8) | Ac- | -GPDN- | -NH$_2$ |
| 3 (SEQ ID NO:6) | biotinyl- | -QKMQ- | -NH$_2$ |
| 4 (SEQ ID NO:8) | biotinyl- | -GPDN- | -NH$_2$ |
| 5 (SEQ ID NO:64) | Ac-GNYRAYA- | -AKKAMMQA- | -AKE-NH$_2$ |
| 6 (SEQ ID NO:65) | Ac-GNYRAYA- | -AKK-NH-(CH$_2$)$_5$-CO-AMMQA- | -AKE-NH$_2$ |
| 7 (SEQ ID NO:66) | Ac-GGNYRAYA- | -AKKAMMKSK-(QKMQ)$_2$-QA- | -AKE-NH$_2$ |
| 8 (SEQ ID NO:67) | Ac-GGNYRAYA- | -AKKAMMKSK-(QKMQ)$_1$-QA- | -AKE-NH$_2$ |
| 9 (SEQ ID NO:68) | Ac-NYRAYA- | -AKKAMMKSK-(QKMQ)$_1$-QA- | -AKE-NH$_2$ |
| 10 (SEQ ID NO:69) | Ac-NYRAYA- | -AKKKSK-(QKMQ)$_1$-AMMQA- | -AKE-NH$_2$ |
| 11 (SEQ ID NO:70) | Ac-GGNYRAYA- | -AKKKSK-(QKMQ)$_1$-AMMQA- | -AKE-NH$_2$ |
| 12 (SEQ ID NO:71) | Ac-GGNYRAYA- | -AKKKSK-(QKMQ)$_2$-AMMQA- | -AKE-NH$_2$ |
| 13 (SEQ ID NO:72) | Ac-GNYRAYA- | -AKKKSK-(QKMQ)$_2$-AMMQA- | -AKE-NH$_2$ |
| 14 (SEQ ID NO:73) | CGNYRAYA- | -AKK-NH-(CH$_2$)$_5$-CO-AMMQA- | -AKE-NH$_2$ |

| COMPOUND | Ξ-PAPIRRR-Z-TEPH-Ψ | -Z- | -Ψ | (Ib) |
|---|---|---|---|---|
| 15 (SEQ ID NO:74) | Ac-RPA | -PGNS- | -AKKKSK-NH$_2$ | |

In the formulae Ia and Ib, the underlined amino acid sequences, corresponding to $E_1$ and $E_2$, represent a minimum epitope of troponin I. The underlined amino acid sequences of Z form with $E_1$ or $E_2$, to which they are linked, an extended epitope of troponin I.

Among the compounds indicated above, compounds 5, 6, 10, 11, 12, 13, 14 and 15 are particularly preferred compounds.

These peptides have the following sequences:

The synthetic biepitope compounds of formula I, which are the subject of the present invention, are obtained by solid phase synthesis according to conventional methods: R. B. Merrifield, *J. Amer. Chem. Soc.* (1963), 85, pp. 2149–2154; R. C. Sheppard, in "*Peptides* 1971", Nesvadba H (ed.) North Holland, Amsterdam, pp. 111; E. Atherton and R. L. Sheppard, in "*Solid phase peptide synthesis, a practical approach*", IRL PRESS, (1989), Oxford University Press, pp. 25–34. As automatic synthesizer, the Millipore 9050 Plus Pep Synthesizer or an equivalent synthesizer can be used.

The solid support used for the syntheses should be compatible with the technique and the chemistry used. For example, for synthesis on the 9050 Plus Pep Synthesizer, it is recommended to use a resin suited to the so-called "continuous flow" technique; the PEG PS resins meet these criteria. These supports consist of a spacer based on polyethylene glycol (PEG) situated between the functional group

```
(SEQ ID NO:27)
Ac-Gly Asn Tyr Arg Ala Tyr Ala Thr Glu Pro His Ala Lys Lys Ala Met Met Gln Ala Leu
     1               5                   10                  15                  20

Leu Gly Ala Arg Ala Lys Glu-NH2
                 25

(SEQ ID NO:28)
Ac-Gly Asn Tyr Arg Ala Tyr Ala Thr Glu Pro His Ala Lys Lys -NH-(CH2)5-CO-Ala Met
     1               5                   10                       15

Met Gln Ala Leu Leu Gly Ala Arg Ala Lys Glu-NH2
         20                  25

(SEQ ID NO:29)
Ac-Asn Tyr Arg Ala Tyr Ala Thr Glu Pro His Ala Lys Lys Lys Ser Lys Gln Lys Met Gln
     1               5                   10                  15                  20

Ala Met Met Gln Ala Leu Leu Gly Ala Arg Ala Lys Glu-NH2
                 25                  30

(SEQ ID NO:30)
Ac-Gly Gly Asn Tyr Arg Ala Tyr Ala Thr Glu Pro His Ala Lys Lys Lys Ser Lys Gln Lys
     1               5                   10                  15                  20

Met Gln Ala Met Met Gln Ala Leu Leu Gly Ala Arg Ala Lys Glu-NH2
                 25                  30                  35

(SEQ ID NO:31)
Ac-Gly Gly Asn Tyr Arg Ala Tyr Ala Thr Glu Pro His Ala Lys Lys Lys Ser Lys Gln Lys
     1               5                   10                  15                  20

Met Gln Gln Lys Met Gln Ala Met Met Gln Ala Leu Leu Gly Ala Arg Ala Lys Glu-NH2
                 25                  30                  35

(SEQ ID NO:32)
Ac-Gly Asn Tyr Arg Ala Tyr Ala Thr Glu Pro His Ala Lys Lys Lys Ser Lys Gln Lys Met
     1               5                   10                  15                  20

Gln Gln Lys Met Gln Ala Met Met Gln Ala Leu Leu Gly Ala Arg Ala Lys Glu-NH2
                 25                  30                  35

(SEQ ID NO:63)
Cys-Gly Asn Tyr Arg Ala Tyr Ala Thr Glu Pro His Ala Lys Lys -NH-(CH2)5-CO-Ala Met
      1               5                   10                       15

Met Gln Ala Leu Leu Gly Ala Arg Ala Lys Glu-NH2
        20                  25

(SEQ ID NO:33)
Ac-Arg Pro Ala Pro Ala Pro Ile Arg Arg Arg Pro Gly Asn Ser Thr Glu Pro His Ala Lys
     1               5                   10                  15                  20

Lys Lys Ser Lys-NH2
``` of the polystyrene of the beads and the point of attachment of the first amino acid. The nature of this point of anchorage may vary according to the C-terminal functional group selected. For example, for a peptide in the form of an amide, a PAL PEG PS type resin may be taken.

The starting resin and the amino acids used as raw material are products which are commercially available (PerSeptive-Biosystem).

The following side chain protecting groups were used:

| Amino acids | Protecting groups |
|---|---|
| Arginine | 2,2,4,6,7-pentamethyl-5-dihydrobenzofuran-sulphonyl (Pbf) |
| Asparagine, Glutamine | Trityl (Trt) |
| Glutamic acid | Tert-butyl ester (otBu) |
| Threonine, Tyrosine | Tert-butyl ether (tBu) |
| Lysine | Tert-butyloxycarbonyl (Boc) |

The primary amine functional group was temporarily protected at the α position of the amino acids with the aid of the 9-fluorenylmethyloxycarbonyl (Fmoc) group. The deprotection is carried out with a 20% piperidine solution in dimethylformamide.

For the coupling, an excess of diisopropylcarbodiimide (DIPCDI) and of 1-hydroxybenzotriazole (HOBt) is preferably used.

After synthesis, the resin is washed with organic solvents (dimethylformamide and then dichloromethane), dried under vacuum and then treated with a trifluoroacetic acid-based solution cooled to 0° C. and containing appropriate scavengers. It will be possible to use, for example, the K reagent containing 82% trifluoroacetic acid, 5% phenol, 5% water, 5% thioanisole and 3% ethanedithiol.

The synthetic biepitope peptides thus isolated are then precipitated and rinsed with ether.

The synthetic biepitope compounds are then purified by reversed-phase liquid chromatography and their purity is determined by mass spectrometry. The Bondapak $C_{18}$ phase can be used, for example, as phase. The peptides are eluted by forming a linear gradient between two buffer solutions, the first of which is essentially aqueous (for example water-TFA 0.1%) and the second of which is rather organic (for example a mixture containing 60% acetonitrile, 40% water and 0.08% TFA). The pure fractions collected are combined, concentrated under vacuum and freeze-dried.

The biepitope character of the compounds of formula I was determined using a troponin I assay kit. It is possible to use, for example, a kit allowing a sandwich-type immunoassay to be used and containing monoclonal antibodies which react with the peptide sequences $E_1$ and $E_2$.

To determine the biepitope character, the compounds of formula I are diluted in the diluent of the kit, which may be for example normal human serum or a buffer solution, and they are assayed like a patient's sample.

The use of compounds of formula I as standard for the immunological assay of troponin I also forms part of the invention.

The present invention also relates to compositions containing the compounds of formula I. They are preferably aqueous solutions or compositions consisting of compounds of formula I in a buffer solution. As buffer solution, it is possible to use, for example, a phosphate buffer solution ($KH_2PO_4/K_2HPO_4$ pH=6.5–7.5) containing Kathon and BSA or Kathon, Régilait and EDTA, or Kathon, Plasmion and optionally EDTA, or Kathon, casein and EDTA.

It is also possible to use succinate buffer (pH=5–6) or Tris-HCl buffer (pH=7.5–8.5) solutions containing Kathon and BSA or Kathon, Régilait and EDTA or Kathon, Plasmion and optionally EDTA, or Kathon, casein and EDTA.

Buffer solutions containing glycine, Kathon, Régilait and EDTA can also be used.

Succinate or phosphate buffer solutions containing Kathon, Régilait and EDTA are preferred.

Kathon®, an antibacterial agent marketed by the company Rhom and Haas, consists of 5-chloro-2-methyl4-isothiazolin-3-one and 2-methyl4-isothiazolin-3-one (1.5%).

Régilait® is marketed by the company Régilait.

Plasmion® is marketed by Bellon Laboratories and consists of modified fluid gelatin (30 g/l), NaCl (5.382 g/l), MgCl (143 mg/l), KCl (373 mg/l), sodium lactate (3.360 g/l), in water.

The following buffer solutions are particularly preferred:
0.1 M succinate buffer solution (pH=6) containing Kathon (0.2%), Régilait (0.05–2%) and 2 mM EDTA,
0.1 M succinate buffer solution (pH=6) containing Kathon (0.2%), casein (0.01–0.5%) and 2 mM EDTA,
0.1 M phosphate butter solution ($KH_2PO_4/K_2HPO_4$) (pH=7.5) containing Kathon (0.2%), Régilait (0.05–0.5%) and 2 mM EDTA,
0.1 M phosphate buffer solution ($KH_2PO_4/K_2PO_4$) (pH=7.5) containing Kathon (0.2%), casein (0.01–0.1%) and 2 mM EDTA.

Compositions containing plasma and a compound of formula I also form part of the present invention.

Immunoassay procedures using, as standards or controls, the compounds of formula I also form part of the invention.

The invention also relates to kits for carrying out immunoassays which include a compound of formula I or a composition which contains a biepitope peptide of formula I.

The following examples illustrate the invention and are given with no limitation being implied.

EXAMPLE 1

Preparation of a Compound According to the Invention (SEQ ID NO: 29).

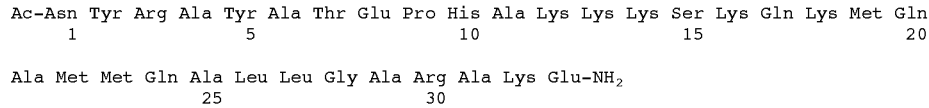

say to be used and containing monoclonal antibodies which react with the peptide sequences $E_1$ and $E_2$.

This peptide was synthesized on a solid phase. The technique developed in 1963 by Merrifield (J. Am. Chem. Soc. (1963), pp. 2149–2154) consists in attaching the first amino acid onto a polymeric solid support (resin) by its acid functional group and in extending the peptide sequence from this first amino acid, the peptide being synthesized remaining anchored onto the resin.

For the synthesis of compound 10, the 9050 Plus Pep Synthesizer was used as synthesizer and the PEG PS resin described above, as resin.

The various steps of the synthesis are summarized in Table I:

TABLE I

| AMINOACID RESIDUE | NH₂ PROTECTION | SIDE PROTECTION | METHOD OF COUPLING | No. of eq-DURATION (DC) |
|---|---|---|---|---|
| Glu | Fmoc | otBu | DIPCDI/HOBt | 5 eq - 30 min |
| Lys | Fmoc | Boc | DIPCDI/HOBt | 5 eq - 30 min |
| Ala | Fmoc | | DIPCDI/HOBt | 5 eq - 30 min |
| Arg | Fmoc | Pbf | DIPCDI/HOBt | 5 eq - 30 min |
| Ala | Fmoc | | DIPCDI/HOBt | 5 eq - 30 min |
| Gly | Fmoc | | DIPCDI/HOBt | 5 eq - 30 min |
| Leu | Fmoc | | DIPCDI/HOBt | 5 eq - 30 min |
| Leu | Fmoc | | DIPCDI/HOBt | 5 eq - 30 min |
| Ala | Fmoc | | DIPCDI/HOBt | 5 eq - 30 min |
| Gln | Fmoc | Trt | DIPCDI/HOBt | 5 eq - 30 min |
| Met | Fmoc | | DIPCDI/HOBt | 5 eq - 30 min |
| Met | Fmoc | | DIPCDI/HOBt | 5 eq - 30 min |
| Ala | Fmoc | | DIPCDI/HOBt | 5 eq - 30 min |
| Gln | Fmoc | Trt | DIPCDI/HOBt | 5 eq - 30 min |
| Met | Fmoc | | DIPCDI/HOBt | 5 eq - 30 min |
| Lys | Fmoc | Boc | DIPCDI/HOBt | 5 eq - 30 min |
| Gln | Fmoc | Trt | DIPCDI/HOBt | 5 eq - 30 min |
| Lys | Fmoc | Boc | DIPCDI/HOBt | 5 eq - 30 min |
| Ser | Fmoc | tBu | DIPCDI/HOBt | 5 eq - 30 min |
| Lys | Fmoc | Boc | DIPCDI/HOBt | 5 eq - 30 min |
| Lys | Fmoc | Boc | DIPCDI/HOBt | 5 eq - 30 min |
| Lys | Fmoc | Boc | DIPCDI/HOBt | 5 eq - 30 min |
| Ala | Fmoc | | DIPCDI/HOBt | 5 eq - 30 min |
| His | Fmoc | Trt | DIPCDI/HOBt | 5 eq - 30 min |
| Pro | Fmoc | | DIPCDI/HOBt | 5 eq - 30 min |
| Glu | Fmoc | otBu | DIPCDI/HOBt | 5 eq - 30 min |
| Thr | Fmoc | tBu | DIPCDI/HOBt | 5 eq - 30 min |
| Ala | Fmoc | | DIPCDI/HOBt | 5 eq - 30 min |
| Tyr | Fmoc | tBu | DIPCDI/HOBt | 5 eq - 30 min |
| Ala | Fmoc | | DIPCDI/HOBt | 5 eq - 30 min |
| Arg | Fmoc | Pbf | DIPCDI/HOBt | 5 eq - 30 min |
| Tyr | Fmoc | tBu | DIPCDI/HOBt | 5 eq - 30 min |
| Asn | Fmoc | Trt | DIPCDI/HOBt | 5 eq - 30 min |
| Acetyl | | | (CH₃CO)₂O/DIEA | 5 eq - 30 min |

At the end of the synthesis, the resin was washed with dimethylformamide, then with dichloromethane and dried under vacuum.

Next, the resin was treated with K reagent (82% trifluoroacetic acid; 5% phenol; 5% water; 5% thioanisole; 3% ethanedithiol). Compound 10 thus isolated by precipitation was then rinsed with diethyl ether. 0.529 g of compound 10 was thus obtained.

In a similar manner, and using the appropriate amino acids, the other compounds of the invention were synthesized.

The molecular weight, evaluated by mass spectrometry, of some compounds of formula Ia and Ib are given below.

| Compound | Molecular weight (Dalton) |
|---|---|
| 1 | 1549.8 |
| 2 | 1545.5 |
| 5 | 3018 |
| 6 | 3132.5 |
| 7 | 4448 |
| 8 | 3934.5 |
| 9 | 3820.5 |
| 10 | 3820.5 |
| 11 | 3934.5 |
| 12 | 4448 |
| 13 | 4391 |
| 15 | 2721 |

EXAMPLE 2

Evaluation of the Immunoreactivity of the Peptides According to the Invention

The biepitope character of the compounds mentioned above was determined using a troponin I assay kit. It is the kit ERIA Troponin I Pasteur Code 79691.

Its principle is based on a sandwich type immunoenzymatic method which allows a quantitative assay of cardiac troponin I in human serum.

The solid phase consists of polystyrene tubes coated with an anti-cardiac troponin I monoclonal antibody (8E1).

The revealing is performed with the aid of a second anti-cardiac troponin I monoclonal antibody (11E12) coupled to peroxidase.

The carrying out of the test comprises the following steps:

The samples and the standards (troponin I standards of animal origin) as well as the peroxidase-coupled monoclonal antibody are incubated in the presence of the anti-cardiac troponin I monoclonal antibody immobilized on the solid phase.

After a series of washes, the enzymatic revealing is carried out by adding the tetramethylbenzidine chromogen.

After stopping the revealing, the optical density is read at $\lambda=450$ nm. The absorbance obtained is directly correlated with the concentration of cardiac troponin I present in a tube.

Compounds 1, 2, 5, 6, 10, 11 and 12 were dissolved in water (C=1 mg/ml or 2 mg/ml depending on the case). These solutions were rediluted using a 0.1 M succinate buffer pH=6 containing 0.05% Régilait and 0.2% Kathon and 2 mM EDTA. The "final solutions" were then assayed as "samples" according to the protocol described above.

Moreover, compounds 1, 2, 10 and 11 were tested after dilution in human serum. In this case, the "final solutions" were obtained by diluting, in normal human serum, aqueous "stock" solutions containing compounds 1, 2, 10 and 11 at a concentration of 2 mg/ml.

All the compounds are reactive in the assay of troponin I.

EXAMPLE 3

Tests of Stability

A compound according to the invention (compound 10) was diluted in water (C=2 mg/ml). From this "stock" solution, four "working" solutions $S_1$, $S_2$, $S_3$ and $S_4$ are obtained.

To carry out the various dilutions, a 0.1 M sodium succinate buffer solution (pH=6) containing Kathon (0.2%), Ré gilait (0.05%) and 2 mM EDTA was used for solutions $S_1$ (C=0.5 ng/ml) and $S_2$ (C=1 ng/ml).

Solutions $S_3$ (C=0.5 ng/ml) and $S_4$ (C=1 ng/ml) were obtained by diluting the "stock" solution with phosphate buffer ($KH_2PO4/K_2HPO_4$ pH=7.5) containing Kathon (0.2%), Régilait (0.05%) and 2 mM EDTA.

Solutions $S_1$, $S_2$, $S_3$ and $S_4$ were assayed, according to the protocol described in Example 2, on D0 (day of preparation of the solutions). The values obtained served as reference for monitoring stability.

Next, solutions $S_1$, $S_2$, $S_3$ and $S_4$ were stored at +4° C. and assayed periodically. During each series of assays, three "control solutions" were used. They are the freeze-dried troponin I control sera distributed in the assay measuring range. For these sera, it was demonstrated beforehand that the storage life of a freeze-dried control serum is greater than 18 months. During each stability test, it was checked that each of the controls tested was obtained at its target concentration. This therefore made it possible to compare the concentrations obtained for the peptides during the various tests. In particular, it was possible to compare the concentration of the solution of the compound according to the invention at D0 (day on which the solution was made) with the concentration of the compound according to the invention during the stability trials over time. The fact that, for the controls, a constant value is always found during the stability trials makes it possible to validate the tests carried out.

The results obtained during the stability trials are indicated in Tables II and III.

TABLE II

| | Absorbance (λ = 450 nm) | | | | |
|---|---|---|---|---|---|
| Solutions | D0 | D + 1 month | D + 2 months | D + 3 months | D + 4 months |
| Blank (C = 0 ng/ml) | 0.00 | 0.00 | 0.01 | 0.00 | 0.03 |
| $S_1$ (C = 0.5 ng/ml) | 0.42 | 0.038 | 0.44 | 0.40 | 0.40 |
| $S_2$ (C = 1.0 ng/ml) | 1.05 | 0.90 | 0.87 | 0.95 | 1.10 |

| | Absorbance (λ = 450 nm) | | | |
|---|---|---|---|---|
| Solutions | D + 1 month/D0 | D + 2 months/D0 | D + 3 months/D0 | D + 4 months/D0 |
| $S_1$ (C = 0.5 ng/ml) | 0.90 | 1.05 | 0.95 | 0.95 |
| $S_2$ (C = 1.0 ng/ml) | 0.86 | 0.83 | 0.90 | 1.05 |

TABLE III

| | Absorbance (λ = 450 nm) | | | | |
|---|---|---|---|---|---|
| Solutions | D0 | D + 1 month | D + 2 months | D + 3 months | D + 4 months |
| Blank (C = 0 ng/ml) | 0.00 | 0.00 | 0.00 | 0.00 | 0.00 |
| $S_3$ (C = 0.5 ng/ml) | 0.27 | 0.23 | 0.27 | 0.25 | 0.28 |
| $S_4$ (C = 1.0 ng/ml) | 0.71 | 0.59 | 0.68 | 0.63 | 0.63 |

| | D + 1 month/D0 | D + 2 months/D0 | D + 3 months/D0 | D + 4 months/D0 |
|---|---|---|---|---|
| $S_3$ (C = 0.5 ng/ml) | 0.85 | 1.00 | 0.93 | 1.04 |
| $S_4$ (C = 1.0 ng/ml) | 0.83 | 0.96 | 0.89 | 0.89 |

The results indicated in Tables I and II demonstrate the excellent stability of the solutions of compound 10 according to the invention.

Trials carried out with other compounds of formula I demonstrated that their stability is comparable to that of compound 10. For example, the trials carried out with compound 6 confirmed that this compound had an excellent stability for at least 9 months, when stored at +4° C. in solution in a 0.1 M sodium succinate buffer solution (pH=6) containing Kathon (0.2%), Régilait (0.2%) and 2 mM EDTA. Compound 6 was dissolved in the buffer indicated above in order to obtain concentrations of 0.25, 4.8 and 18 ng/ml.

This stability study was validated with the aid of compound 6 stored at −20° C. and used as reference.

It was checked beforehand that compound 6 is stable when stored at −20° C. for at least 18 months. The results of this trial are given in Table IV.

TABLE IV

| | Concentration in ng/ml | | | | | | | |
|---|---|---|---|---|---|---|---|---|
| Solutions | D0 | D + 1 month | D + 2 months | D + 3 months | D + 4 months | D + 5 months | D + 6 months | J + 9 months |
| Solution 1 | 0.26 | 0.29 | 0.24 | 0.24 | 0.23 | 0.25 | 0.23 | 0.22 |
| Solution 2 | 4.93 | 5.25 | 4.58 | 4.77 | 4.57 | 4.42 | — | 3.87 |
| Solution 3 | 18.21 | 19.61 | 16.79 | 17.48 | 16.35 | 17.21 | 16.13 | 15.04 |

What is claimed is:

1. Biepitope compound consisting of formula I:

$$\Xi-E_1-Z-E_2-\Psi \quad (I)$$

in which:

$E_1$ and E2, which are identical or different, represent a peptide sequence comprising a minimum epitope of troponin I, Z represents
a chain of formula II:

$$-NH-(CH_2)_m-CO- \quad (II)$$

in which m represents an integer from 1 to 10, or a mixed construct of formulae III to V:

$$\text{-}[pep_1\text{-}NH-(CH_2)_m-CO]_p\text{-} \quad (III)$$

$$\text{-}[pep_1\text{-}NH-(CH_2)_m-CO\text{-}pep_2]_p\text{-} \quad (IV)$$

$$\text{-}[NH-(CH_2)_m-CO\text{-}pep2]_p\text{-} \quad (V)$$

in which m represents an integer from 1 to 10, p represents an integer from 1 to 5, and $pep_1$ and $pep_2$ which are identical or different, represent a peptide chain containing from 2 to 10 amino acids forming an extended epitope of troponin I with the sequences $E_1$ an $E_2$, respectively, Ξ represents a hydrogen atom, an acetyl group, a peptide sequence of 1 to 10 amino acids, an N-α-acetylated peptide sequence of 1 to 10 amino acids, a cysteinyl, biotinyl or biocytinyl group, a peptide sequence of 1 to 10 amino acids carrying a cysteinyl, biotinyl or biocytinyl residue, a linear or branched amino($C_1$–$C_{10}$ alkyl)carbonyl chain, an N-α-acetylated linear or branched amino($C_1$–$C_{10}$ alkyl)carbonyl chain, a mixed construct of at least one peptide sequence of 1 to 10 amino acids and at least one linear or branched amino($C_1$–$C_{10}$ alkyl)carbonyl chain, or a mixed construct of at least one peptide sequence of 10 to 10 amino acids and at least one linear or branched amino($C_1$–$C_{10}$ alkyl)carbonyl chain carrying a cysteinyl, biotinyl, or biocytinyl residue, Ψ represents a hydroxyl radical, an amino radical, a peptide sequence of 1 to 10 amino acids, or a peptide sequence of 1 to 10 amino acids carrying an amino-terminal group, a linear or branched amino($C_1$–$C_{10}$ alkyl)carbonyl chain, a linear or branched amino($C_1$–$C_{10}$ alkyl)carbonyl chain carrying a hydroxyl radical or an amino radical, a mixed construct of at least one peptide sequence of 1 to 10 amino acids and at least one linear or branched amino($C_1$–$C_{10}$ alkyl)carbonyl chain, or a mixed construct of at least one peptide sequence of 1 to 10 amino acids and at least one linear or branched amino($C_1$–$C_{10}$ alkyl)carbonyl chain carrying a hydroxyl radical or an amino radical.

2. The biepitope compound according to claim 1, in which $E_1$ and/or $E_2$, which are identical or different, represent a peptide sequence selected from the group consisting of SEQ ID NO: 1 -Thr Glu Pro His-, SEQ ID NO: 2 -His Ala Lys Lys-, SEQ ID NO: 3 -Pro Ala Pro IIe Arg Arg Arg- SEQ ID NO: 4 -Leu Leu Gly Ala Arg, and SEQ ID NO: 5 -Arg Lys Asn IIe-.

3. The biepitope compound according to claim 1 of formulae Ia or Ib:

Ξ-Thr Glu Pro His-Z-Leu Leu Gly Ala Arg-Ψ (Ia)

Ξ-Pro Ala Pro IIe Arg Arg Arg-Z-Thr Glu Pro His-Ψ (Ib)

in which

Z includes sequence

SEQ ID NO: 26 -Ala Lys Lys-NH—$(CH_2)_m$—CO-Ala Met Met Gln Ala-, wherein m represents an integer from 1 to 10, Ξ represents an acetyl radical, a cysteinyl radical, or a biotinyl or biocytinyl radical optionally linked with a peptide sequence residue selected from the group consisting of:

SEQ ID NO: 57 -Gly A Tyr Arg Ala Tyr Ala-,

SEQ ID NO: 58 -Gly Gly Asn Tyr Arg Ala Tyr Ala-,

SEQ ID NO: 59 -Asn Tyr Arg Ala Tyr Ala-, and

SEQ ID NO: 60 -Arg Pro Ala- and

Ψ represents an amino radical or a peptide sequence selected from the group consisting of SEQ ID NO: 61 -Ala Lys Glu and SEQ ID NO: 62 -Ala Lys Lys Lys Ser Lys.

4. The biepitope compound according to claim 1, selected from the group consisting of

```
Ac-Gly Asn Tyr Arg Ala Tyr Ala Thr Glu Pro His Ala Lys Lys-NH(CH₂)₅—CO-ala Met
    1               5                   10                  15

Met Gln Ala Leu Leu Gly Ala Arg Ala Lys Glu-NH₂ (SEQ ID NO:28)
        20                  25
``` and

```
Cys-Gly Asn Tyr Arg Ala Tyr Ala Thr Glu Pro His Ala Lys Lys-NH(CH₂)—CO-Ala Met
    1               5                   10                  15

Met Gln Ala Leu Gly Ala Arg Ala Lys Glu-NH₂ (SEQ ID NO:53).
        20              25
```

5. Composition containing the biepitope compound according to claim 1 in solution in water, in plasma, or in a buffer solution.

6. Composition according to claim 5, wherein the buffer solution is selected from the group consisting of phosphate, succinate, and Tris-HCl buffer solutions.

7. Composition according to claim 5, wherein the buffer solution is selected from the group consisting of a succinate buffer solution pH=5–6 containing Kathon, Régilait, and EDTA, a succinate buffer solution pH=5–6 containing Kathon, casein, and EDTA, a phosphate buffer solution $KH_2PO_4/K_2HPO_4$ 0.1 M and pH=6.5–7.5 containing Kathon, Régilait and EDTA, and a phosphate buffer solution $KH_2PO_4/K_2HOP_4$ 0.1 M pH=6.5–7.5 containing Kathon, casein, and EDTA.

8. A method for immunoassaying troponin I, wherein the biepitope compound according to claim 1 is used as a standard.

9. The method according to claim 8, wherein the immunoassay is a sandwich immunoassay.

10. A kit for carrying out an immunoassay comprising (a) the biepitope compound according to claim 1 or (b) a composition containing the biepitope compound in solution in water, in plasma, or in a buffer solution.

* * * * *